United States Patent [19]

Ruderian

[11] Patent Number: 4,640,284

[45] Date of Patent: Feb. 3, 1987

[54] HOT AND COLD DIRECT CONTACT APPLICATOR

[76] Inventor: Max J. Ruderian, 545 Hanley Ave., W. Los Angeles, Calif. 90049

[21] Appl. No.: 757,380

[22] Filed: Jul. 22, 1985

[51] Int. Cl.⁴ .............................................. A61F 7/00
[52] U.S. Cl. ........................................ 128/399; 62/3; 62/293; 126/204
[58] Field of Search ...................... 128/399; 126/204; 136/203, 204; 62/3, 293

[56] References Cited

U.S. PATENT DOCUMENTS

Re. 26,276 10/1967 Hirschhorn ........................... 62/3 X
3,133,539 5/1964 Eidus .................................... 128/399

Primary Examiner—Anton O. Oechsle
Attorney, Agent, or Firm—Kelly, Bauersfeld & Lowry

[57] ABSTRACT

A therapeutic device for applying structures in direct contact with the skin of the human body to heat and to cool the same. A hot plate and a cool plate are provided on opposite sides of conventional electrical means to produce the heating and cooling. A plurality of vanes normal to the hot plate are fixed thereto and extend to an auxiliary plate to which they are also fixed. The vanes and the auxiliary plate aid in reducing the temperature of the hot plate and thereby aid in reducing the temperature of the cold plate. A fabric sock having differently weighted swatch portions for different thermal insulation surrounds the cold and auxiliary plates. A fan cools the vanes. A tray shaped body support is provided with holes to permit the escape of warm air produced by the fan.

5 Claims, 7 Drawing Figures

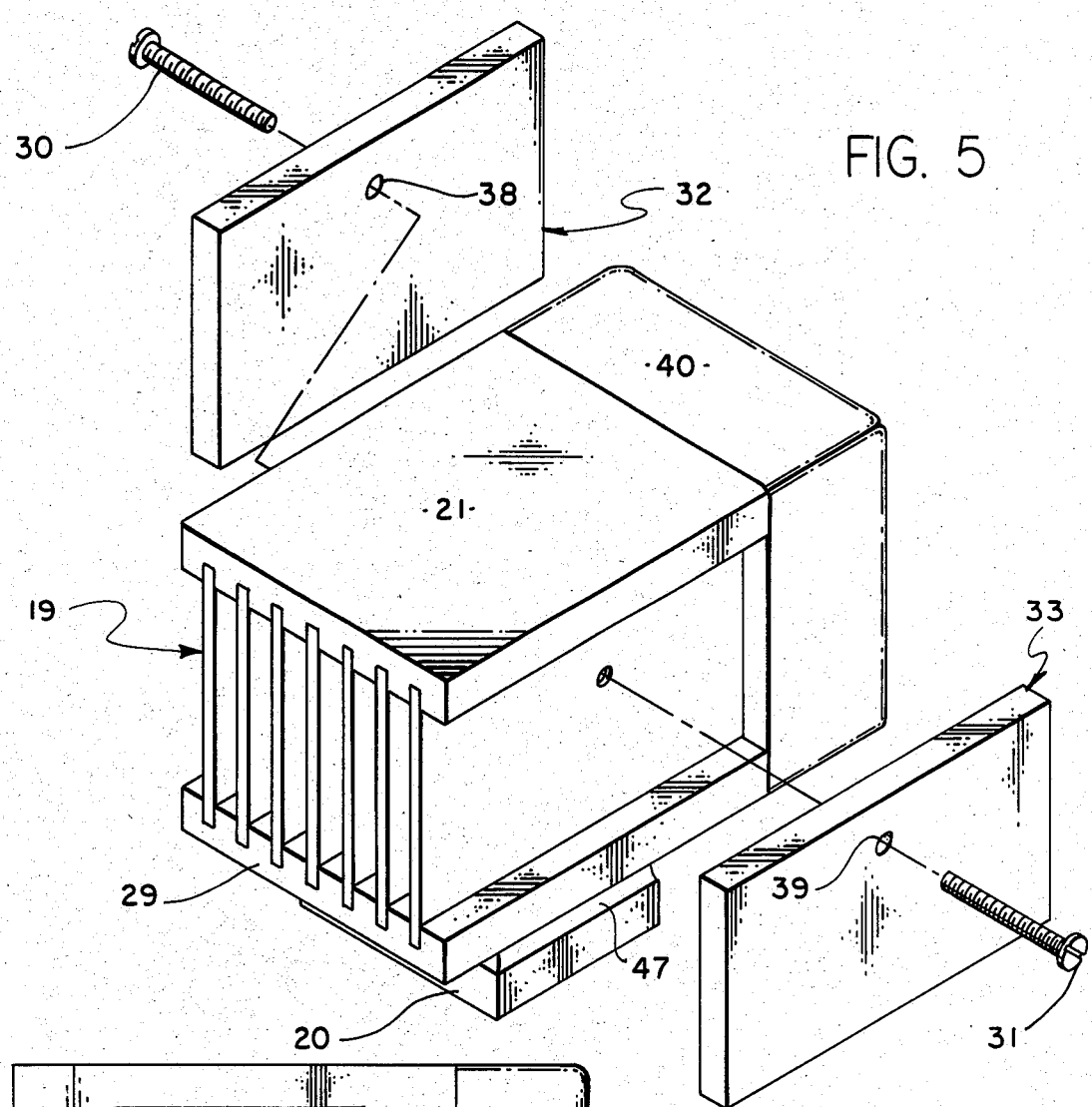
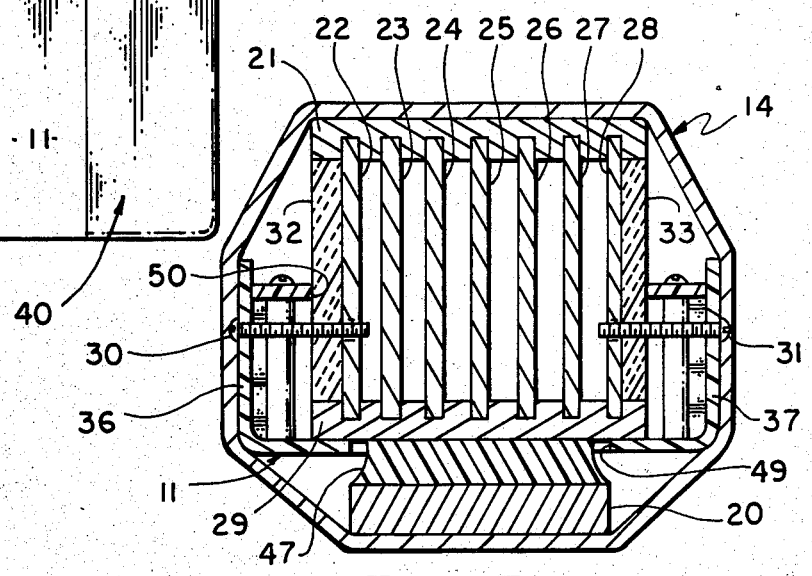
FIG. 5
FIG. 6
FIG. 7

HOT AND COLD DIRECT CONTACT APPLICATOR

FIELD OF THE INVENTION

This invention relates generally to therapeutic devices and more particularly to a therapeutic applicator having plates to be applied directly to the human body which are respectively hot and cold.

BACKGROUND OF THE INVENTION

In my co-pending patent applications identified as follows:

Ser. No. 06/701,745 filed 2-14-85 for SALVE APPLICATOR now U.S. Pat. No. 4,596,565; and Ser. No. 06/702,800 filed 2-19-85 for MASSAGING DEVICE:

there are disclosed various therapeutic devices in the form of massaging units wherein heated air is passed through an applicator surface to a person's skin while massaging is taking place. Vibrating means may constitute an integral part of the applicator as well as means for applying a medicant to the applicator surface.

I have found that in addition to the excellent therapeutic results realizable by the various units described in the above applications, treatment of an area with the direct application of a warm plate and thereafter a cold plate, and then again the warm plate and then again the cold plate, the same separately, alternately, or otherwise can provide very beneficial results. This hot-cold application is similar to treatments wherein a person wil enter a hot sauna and then a cool pool and then back into a hot sauna. Usually the warm plate is applied about one and one-half times as long as the cold plate is applied.

To the best of my knowledge, there is presently no massaging unit or therapeutic device available which can provide for a hot and cold therapeutic treatment except by an air treatment disclosed in my co-pending application Ser. No. 719,063 filed Apr. 2, 1985, for HOT AND COLD THERAPEUTIC APPLICATOR now U.S. Pat. No. 4,587,959.

BRIEF DESCRIPTION OF THE PRESENT INVENTION

With the foregoing in mind, the present invention contemplates the provision of a therapeutic applicator in which warm and cold plates can be applied directly to the skin during a massaging operation in an alternate manner and by a single unit.

In accordance with the present invention, a therapeutic device is provided for applying the plates directly against the human body to heat and to cool the same. A hot plate and a cool plate are provided on opposite sides of conventional electrical means to produce the heating and cooling.

A plurality of vanes normal to the hot plate are thermally bonded thereto and extend to an auxiliary plate (a warm plate) to which they are also thermally bonded. The vanes and the auxiliary plate aid in reducing the temperature of the hot plate and thereby aid in reducing the temperature of the cold plate. A sock having differently weighted fabrics for different heat transfers surrounds the cold and auxiliary plates.

A fan cools the vanes.

A support is provided with holes to permit the escape of warm air produced by the fan.

BRIEF DESCRIPTION OF THE DRAWINGS

A better understanding of this invention as well as further features and advantages thereof will be had by now referring to the accompanying drawings in which:

FIG. 5 is an exploded perspective view of the hot and cold plate assembly;

FIG. 6 is a bottom plan view of the hot and cold plate assembly; and

FIG. 7 is a vertical sectional view through the applicator of FIG. 2 taken on the line 7—7 therein.

DETAILED DESCRIPTION OF THE PREFERRED EMBODIMENT

Figure 1:
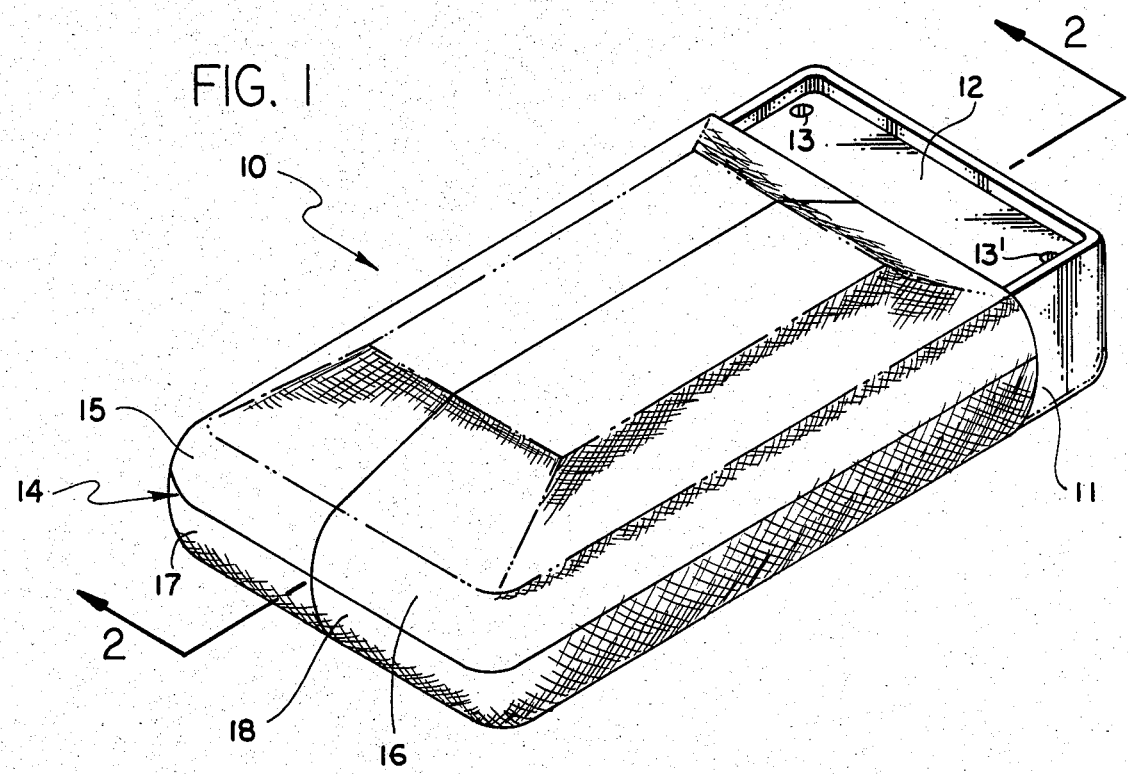
FIG. 1 is a perspective view of the direct hot and cold contact therapeutic applicator of this invention.

In the drawing in FIG. 1, the hot and cold applicator of the present invention is shown at 10 including a tray shaped body 11, a cover plate 12 fixed to body 11 with screws 13 and 13' and a cloth fabric sock 14 having swatch portions 15, 16, 17 and 18 of different corresponding thermal insulation properties.

Figure 2:
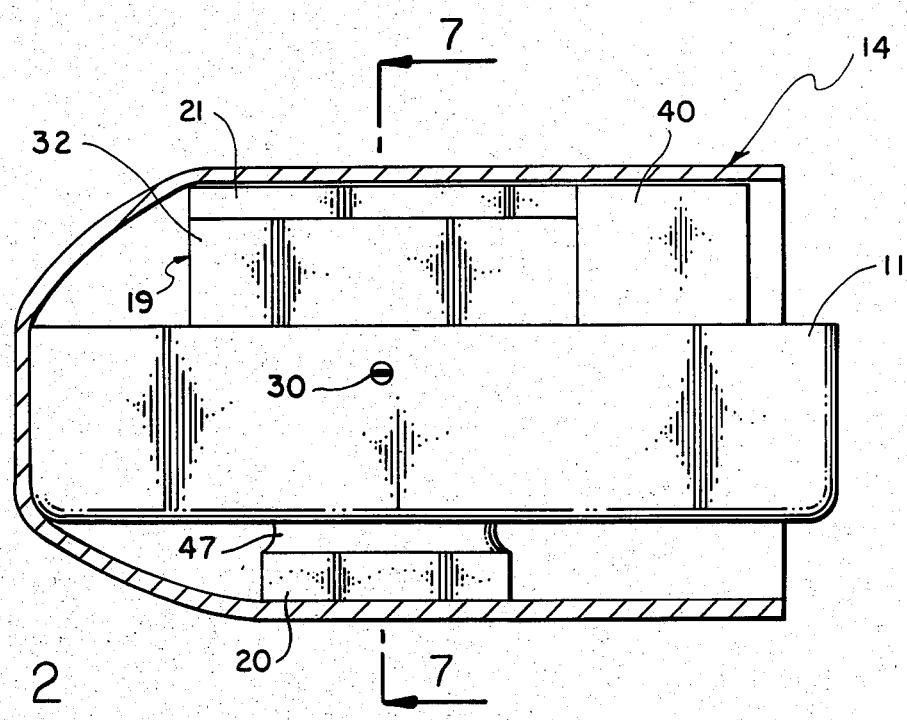
FIG. 2 is a side elevational view thereof, partly in section, taken on line 2—2 of FIG. 1.

In FIG. 2, a hot and cold assembly 19 is shown fixed within the tray shaped body or "boat" 11. Assembly 19 includes a cold aluminum plate 20, a warm auxiliary aluminum plate 21, and aluminum vanes 22, 23, 24, 25, 26, 27 and 28 conductively bonded (thermally at least) both to auxiliary plate 21 and to a hot plate 29 (FIG. 7).

Screws 30 and 31 (FIGS. 2 and 7) hold assembly 19 within boat 11 between insulator blocks 32 and 33. Screws 30 and 31 are thus threaded into tapped holes in vanes 22 and 28, respectively, and are slidable through respective corresponding accommodating holes 34 and 35 in walls 36 and 37 of boat 11 (FIG. 4,) and through respective corresponding accommodating holes 38 and 39 in insulator blocks 32 and 33 (FIG. 5).

Figure 3:
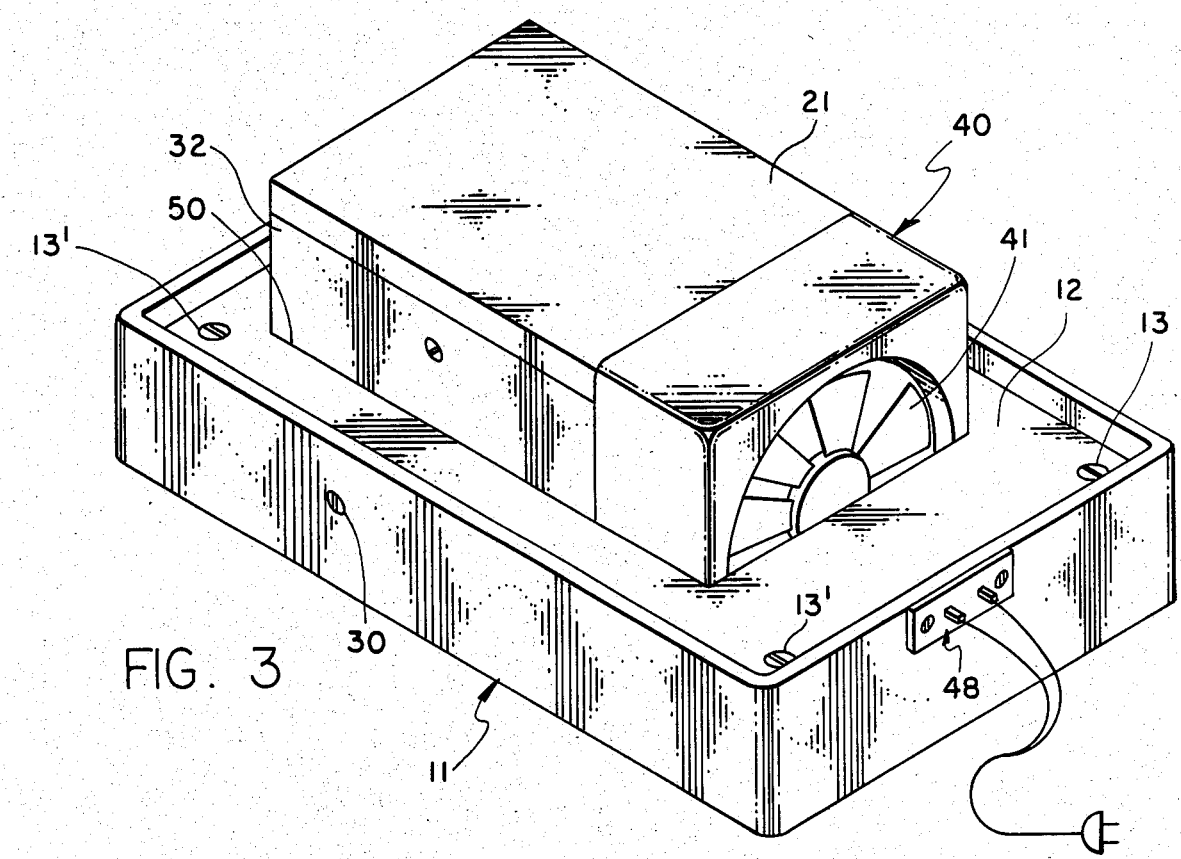
FIG. 3 is another perspective view of the applicator without the sock.
Figure 4:
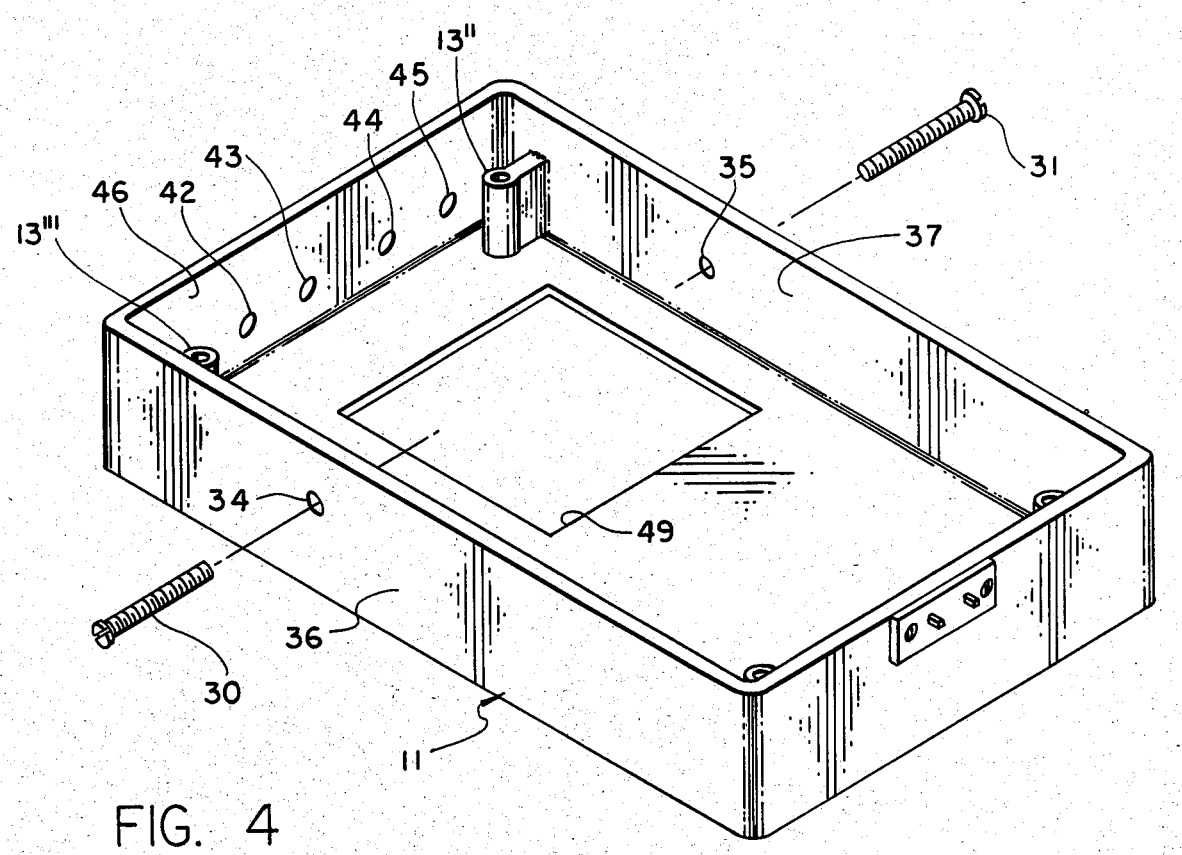
FIG. 4 is an exploded perspective view of an apertured tray shaped body or "boat" to support a hot and cold plate assembly.

A per se conventional fan assembly 40 including a fan 41 is fixed to hot and cold assembly 19 as shown in FIGS. 2, 3 and 5. Fan 41 circulates air into the spaces between immediately adjacent pairs of the vanes 22-28 and outwardly of holes 42, 43, 44 and 45 through an end wall 46 of boat 11 (FIG. 4).

Hot plate 29 (FIG. 7) without the grooves for vanes 22-28, with cold plate 20 and electrical layer 47 may be entirely conventional to cause plate 20 to be cold and to cause plate 29 to be hot. See all of FIGS. 2, 5 and 7. Plates 20 and 29 are thus thermally bonded to layer 47.

Electrical power is supplied to the motor (not shown) of fan 41 in assembly 40 and to layer 47 via a conventional terminal assembly 48 shown in FIG. 3.

Boat 11 contains an aperture 49 (FIG. 4) outwardly of which layer 47 and cold plate 20 project. See FIGS. 2, 5 and 7.

As shown in FIG. 4, boat 11 has internal appendages 13" and 13'" into which screws 13 and 13' are threaded.

As shown in FIGS. 3 and 7, cover plate 12 has a rectangular aperture 50 upwardly through which hot and cold assembly 19 and fan assembly 40 can project.

SUMMARY

The way that the device of the present invention works is based on a highly technical but simple system.

The system uses a space age electronic module approximately 2½"×2½" which has the capabilities of having a hot side and a cold side due to the flow of electrons and a percentage of electric current by opposing electron flow against the hole flow pockets.

When a 12 volt dc voltage is applied to the module, the reaction is that one side is hot and the other side cold.

In order to maintain and to keep this effect, the hot side (plate 29) is sunk into an aluminum heat sink block which has vanes 22-28 attached to it.

A fan motor also being energized by 12 volts passes ambient air between vanes 22-28 so that the hot side will always act as a heat sink. By doing so, the reaction of the cold side is to go colder. This hot and cold are resultant reactions.

If the heat is not dissipated enough, then the cold side will not drop as cold. This device has operating temperatures of approximately 29° F. (cold plate 20) and 120° F. (auxiliary plate 21).

By having this we now have a way of producing a hot and cold application for muscular and many more applications for medical therapy treatment. Bruises may be treated where the treatment is cold for swelling and hot for pain. But there are going to be many ways of using this device for medical treatments.

The present invention may be described as a hot and cold direct contact applicator comprising: hot and cold parallel thermally conductive plates 29 and 20 defining a space therebetween.

Layer 47 is actuable by a voltage applied thereto to cause heat to be withdrawn from cold plate 20 and to cause heat to be added to said hot plate 29.

Thermally conductive auxiliary plate 21 is parallel to the hot and cold plates 29 and 20.

Parallel aluminum vanes are fixed between and to hot and auxiliary plates 29 and 21 to act as a heat sink and to dissipate at least some of the heat retained in hot plate 29.

Note that vanes 22-28 define spaces therebetween, hot plate 29 and auxiliary plate 21 having facing parallel flat surfaces.

Vanes 22-28 are flat and normal to flat surfaces of hot plate 29 and auxiliary plate 21.

Auxiliary plate 21 is maintained at a temperature which is above that of cold plate 20 and which is below that of hot plate 29.

Fabric sock 14 is positioned around and in proximity to cold and auxiliary plates 20 and 21. The sock 14 has different corresponding thermal insulation to be rotated to selected positions over plates 20 and 21.

Fan 41 is fixed relative to vanes 22-28 at one end thereof to blow air into the spaces therebetween from right to left as viewed in FIG. 2.

Body 11 is tray shaped body. Body 11 is fixed relative to plates 20, 21 and 29 and vanes 22-28 and cover plate 12 is provided to fit over body 11.

From all of the foregoing, it will be evident that the present invention has provided a very versatile therapeutic applicator wherein hot and cold treatments can be alternately applied to provide further therapeutic benefits.

What is claimed is:

1. A hot and cold direct contact applicator comprising:
   hot and cold parallel thermally conductive plates defining a space therebetween;
   circuit means fixed to said hot and cold plates in said space between the same;
   said circuit means being actuable by a voltage applied thereto to cause heat to be withdrawn from said cold plate and to cause heat to be added to said hot plate;
   a thermally conductive auxiliary plate parallel to said hot and cold plates;
   a plurality of thermally conductive parallel vanes fixed between and to said hot and auxiliary plates to act as a heat sink and dissipate at least some of the heat retained in said hot plate, said vanes defining spaces therebetween; and
   a fabric sock positioned around said cold and auxiliary plates, said sock having different circumferential swatch portions of different corresponding thermal insulation.

2. The invention as defined in claim 1, wherein:
   said hot plate and said auxiliary plate have facing parallel flat surfaces,
   said vanes being flat and normal to said hot plate and auxiliary plate flat surfaces.

3. The invention as defined in claim 1, wherein:
   a fan is fixed relative to said vanes at one end thereof to blow air into the spaces therebetween,
   a tray shaped body is fixed relative to said plates and vanes, and
   a cover plate is provided to fit over said body,
   said body having holes through one wall thereof to permit the flow of air outwardly of the spaces between said vanes at the other end thereof,
   said body having an aperture through which said cold plate projects,
   said cover plate having an aperture through which said vanes project.

4. A hot and cold direct contact applicator, comprising:
   hot and cold parallel thermally conductive plates defining a space therebetween;
   circuit means fixed to said hot and cold plates in said space between the same;
   said circuit means being actuable by a voltage applied thereto to cause heat to be withdrawn from said cold plate and to cause heat to be added to said hot plate;
   a thermally conductive auxiliary plate parallel to said hot and cold plates;
   a plurality of thermally conductive parallel vanes fixed between and to said hot and auxiliary plates to act as a heat sink and to dissipate at least some of the heat retained in said hot plate, said vanes defining spaces therebetween;
   a fan fixed relative to said vanes at one end thereof to blow air into the spaces therebetween;
   a tray shaped body fixed relative to said plates and vanes; and
   a cover plate provided to fit over said body;
   said body having holes through one wall thereof to permit the flow of air outwardly of the spaces between said vanes at the other end thereof;
   said body having an aperture through which said cold plate projects;
   said cover plate having an aperture through which said vanes project.

5. The invention as defined in claim 4, wherein:
   said hot plate and said auxiliary plate have facing parallel flat surfaces,
   said vanes being flat and normal to said hot plate and auxiliary plate flat surfaces.

* * * * *